United States Patent
Russell et al.

(10) Patent No.: US 9,786,061 B2
(45) Date of Patent: Oct. 10, 2017

(54) SPECIMEN VALIDITY ANALYSIS SYSTEMS AND METHODS OF OPERATION

(71) Applicant: GENPRIME, INC., Spokane, WA (US)

(72) Inventors: Michael Arthur Russell, Spokane, WA (US); Claire Elizabeth Norton, Spokane, WA (US); Darby Dawn McLean, Spokane Valley, WA (US); Jason Buck Somes, Spokane, WA (US)

(73) Assignee: GENPRIME, INC., Spokane, WA (US)

( * ) Notice: Subject to any disclaimer, the term of this patent is extended or adjusted under 35 U.S.C. 154(b) by 109 days.

(21) Appl. No.: 15/014,920

(22) Filed: Feb. 3, 2016

(65) Prior Publication Data
US 2016/0225165 A1    Aug. 4, 2016

Related U.S. Application Data

(60) Provisional application No. 62/111,418, filed on Feb. 3, 2015.

(51) Int. Cl.
G06T 7/00 (2017.01)
G06T 7/40 (2017.01)
G01N 21/84 (2006.01)
G06T 7/90 (2017.01)

(52) U.S. Cl.
CPC ......... *G06T 7/408* (2013.01); *G01N 21/8483* (2013.01); *G06T 7/0012* (2013.01); *G06T 7/90* (2017.01); *G06T 2207/10024* (2013.01); *G06T 2207/30024* (2013.01)

(58) Field of Classification Search
CPC ....... G06T 7/0002; G06T 7/0012; G06T 7/90; G06T 2207/10024; G06K 9/6201; G06K 9/6215; G01N 21/17; G01N 21/1765; G01N 21/25; G01N 21/27; G01N 21/29; G01N 2021/7759; G01N 2021/7793; G01N 21/78; G01N 21/8483; G01N 2021/8488
See application file for complete search history.

(56) References Cited

U.S. PATENT DOCUMENTS

| | | | | |
|---|---|---|---|---|
| 2013/0330831 A1* | 12/2013 | Morrow et al. | ....... | G01N 21/78 436/169 |
| 2015/0211987 A1* | 7/2015 | Burg et al. | ............. | G01N 21/27 356/402 |
| 2016/0080548 A1* | 3/2016 | Erickson et al. | . | H04M 1/72527 455/556.1 |

* cited by examiner

*Primary Examiner* — Andrew W Johns
(74) *Attorney, Agent, or Firm* — Seed IP Law Group LLP

(57) ABSTRACT

A specimen analysis system includes at least one processor to receive a set of image information that represents an image of at least a specimen validity portion of the specimen test article which includes at least one optical specimen validity marker, the color of which indicates the validity of the specimen; determine a set of color component values for one or more of a plurality of pixels of the image that are representative of the specimen validity portion of the specimen test article, the set of color component values including at least three color component values; and assess at least one specimen validity characteristic of the specimen based at least in part on each color component value of the determined set of color component values for the one or more of the plurality of pixels of the image.

40 Claims, 4 Drawing Sheets

400

| REFERENCE COLOR COMPONENT VALUES | SPECIMEN VALIDITY CHARACTERISTIC |
|---|---|
| 50, 40, 30 | RESULT A |
| 100, 100, 100 | RESULT B |
| 150, 200, 220 | RESULT C |

| REFERENCE COLOR COMPONENT VALUES | PHYSICAL CHARACTERISTIC VALUE | SPECIMEN VALIDITY STATUS |
|---|---|---|
| 20, 34, 40 | VALUE 1 | INVALID |
| 50, 40, 30 | VALUE 2 | VALID |
| 100, 100, 100 | VALUE 3 | VALID |
| 150, 200, 220 | VALUE 4 | INDETERMINATE |

*FIG. 5*

SPECIMEN VALIDITY ANALYSIS SYSTEMS AND METHODS OF OPERATION

BACKGROUND

Technical Field

The present disclosure generally relates to specimen analysis systems and, more particularly, to specimen analysis systems that optically assess specimen test articles such as lateral flow strips.

Description of the Related Art

Specimen test articles may be used to determine a presence or absence of a test subject substance in a specimen (i.e., the principal substance for which the specimen is being tested). In particular, certain specimen test articles (e.g., lateral flow strips) include at least one optical test substance marker that optically indicates at least the presence or absence of the test subject substance in the specimen. For example, a color of the optical test substance marker may indicate the presence or absence of the test subject substance within the specimen. As one example, a color of the optical test substance marker may remain unchanged from a first color if the specimen does not contain the test subject substance, while the color of the optical test substance marker changes from the first color to a second, different color if the test subject substance is present within the specimen.

BRIEF SUMMARY

Specimen test articles may also include at least one optical specimen validity marker in addition to the optical test substance marker. A color of the optical specimen validity marker indicates a validity of the specimen. As one example, the optical specimen validity marker may change colors in the presence of an adulterant, where the presence of an adulterant renders the specimen invalid. As another example, the optical specimen validity marker may remain the same color in the absence of a particular substance in the specimen, where the absence of the particular substance in the specimen renders the specimen invalid.

As yet another example, the optical specimen validity marker may change colors to indicate a value or status of a physical characteristic of the specimen, such as pH, specific gravity, temperature, or other characteristics. The validity of the specimen may be inferable or determinable in view of the indicated value or status of the physical characteristic.

Specimen test articles may also include a control marker that simply indicates whether the specimen test article properly absorbed or otherwise received the specimen.

A human tester using the specimen test article to test for the test subject substance may manually view the specimen test article and attempt to determine the test results. However, this requires the human tester to manually determine the respective colors of the test substance marker and the specimen validity marker and to manually determine the results of the test from such colors. Such process may result in an undesirably high number of errors. For example, the human tester may incorrectly interpret the color of one or more markers, particularly for markers that provide a plurality or a spectrum of colors which indicate different results. As another example, the human tester may confuse one marker for another or otherwise incorrectly translate the colors of the markers into results of the test. Therefore, specimen analysis systems that automatically assess at least one specimen validity characteristic of a specimen are desirable.

Specimen validity analysis systems and method of operation of the present disclosure advantageously optically assess specimen test articles to assess at least one specimen validity characteristic of a specimen. In particular, one example specimen analysis system includes at least one processor to receive a set of image information that represents an image of at least a specimen validity portion of the specimen test article which includes at least one optical specimen validity marker, the color of which indicates the validity of the specimen. The processor determines a set of color component values for one or more of a plurality of pixels of the image that are representative of the specimen validity portion of the specimen test article and assesses at least one specimen validity characteristic of the specimen based at least in part on each color component value of the determined set of color component values for the one or more of the plurality of pixels of the image.

According to an aspect of the present disclosure, the set of color component values determined for the one or more pixels representative of the specimen validity portion of the specimen test article includes at least three color component values. As one example, the set of color component values includes a red color component value, a green color component value, and a blue color component value. Through the use of three or more color component values, for example, the color of the specimen validity portion of the specimen test article is more fully described than with use of two or fewer color component values. For example, use of only two or fewer color component values ignores or otherwise does not permit description of a large number of colors. Therefore, use of three or more color component values allows for more exact analysis of the color of the specimen validity portion of the specimen test article.

According to another aspect of the present disclosure, the specimen analysis system respectively compares the determined set of color component values with a plurality of sets of reference color component values to identify a first set of reference color component values that is closest or most comparable to the determined set of color component values. Each set of reference color component values can include at least three reference color component values and can be logically associated (e.g., in a lookup table) with one or more specimen validity characteristic results or statuses, physical characteristic values, and/or other information. More particularly, each set of reference color component values and its corresponding relationships can have been determined through testing or calibration of the corresponding variety of specimen test article using reference specimens having known specimen validity characteristics and/or physical characteristic values.

After identifying the first set of reference color component values that is closest to the determined set of color component values, the specimen analysis system can select the specimen validity characteristic result or status, physical characteristic value, or other information associated with such first set of reference color component values as pertaining to the specimen. For example, if the first set of reference color component values is logically associated with a particular pH value, then the system can determine that the specimen has such particular pH value and, for example, assess the validity of specimen based on such particular pH value (e.g., by selecting a specimen validity status logically associated with such particular pH value in a lookup table or by calculating a specimen validity status by inputting the particular pH value into one or more analytical equations).

Thus, through the use of appropriately constructed sets of reference color component values, the systems and methods of the present disclosure enable determination of specimen validity characteristics without requiring interpolation of potential results. More particularly, it may be possible to identify two potential results and determine the test result through interpolation of the two potential results.

However, interpolation of potential results may provide an erroneous result if the value or status of the characteristic being tested does not change linearly between the two potential results (e.g., if the color of the marker being assessed does not change proportionally relative to the characteristic being tested). In addition, if the increment or interval between the two potential results is relatively large, interpolation of the two potential results may not accurately reflect the true value or status of the specimen being tested. As such, the systems and methods of the present disclosure advantageously allow automatic assessment of at least one specimen validity characteristic without requiring interpolation.

A specimen analysis system to analyze specimen test articles which include at least one optical test subject substance marker that indicates at least a presence or an absence of a test subject substance in a specimen, and at least one optical specimen validity marker, a color of which indicates a validity of the specimen may be summarized as including at least one processor; and at least one non-transitory processor-readable medium that is communicatively coupled to the at least one processor and that stores at least one of processor-executable instructions or data that, when executed by the at least one processor, cause the at least one processor to: receive a set of image information that represents an image of at least a specimen validity portion of the specimen test article which includes the at least one optical specimen validity marker, the color of which indicates the validity of the specimen; determine a set of color component values for one or more of a plurality of pixels of the image that are representative of the specimen validity portion of the specimen test article, the set of color component values comprising at least three color component values, each of the color component values representative of an amount of a respective color component of a color of the corresponding one or more of the plurality of pixels of the image; and assess at least one specimen validity characteristic of the specimen based at least in part on each color component value of the determined set of color component values for the one or more of the plurality of pixels of the image. To determine a set of color component values, the processor may determine a red color component value, a green color component value, and a blue color component value. To assess at least one specimen validity characteristic of the specimen, the processor may assess the at least one specimen validity characteristic based at least in part on each of a red color component value, a green color component value, and a blue color component value. To assess at least one specimen validity characteristic of the specimen, the processor may assess at least a first specimen validity characteristic based at least in part on each of a first red color component value, a first green color component value, and a first blue color component value of a first one of the at least one optical specimen validity marker, and may assess at least a second specimen validity characteristic based at least in part on each of a second red color component value, a second green color component value, and a second blue color component value of a second one of the at least one optical specimen validity marker. Execution of the at least one of the processor-executable instructions or data may cause the at least one processor to assess the presence or the absence of one or more of oxidants, creatinine, nitrite, and aldehydes in the specimen.

Execution of the at least one of the processor-executable instructions or data may further cause the at least one processor to: assess the presence or the absence of the test subject substance in the specimen based at least in part on the at least one optical test subject substance marker. Execution of the at least one of the processor-executable instructions or data may cause the at least one processor to assess the presence or the absence of alcohol, cocaine, marijuana, amphetamines, performance enhancing drugs, substances indicative of use of alcohol, cocaine, marijuana, amphetamines, or performance enhancing drugs, or derivatives of alcohol, cocaine, marijuana, amphetamines, or performance enhancing drugs in the specimen. The specimen test article may be a lateral flow strip, and the at least one optical test subject substance marker that indicates at least the presence or the absence of the test subject substance in the specimen may be spaced on the lateral flow strip from the at least one optical specimen validity marker, the color of which indicates the validity of the specimen.

The specimen analysis system may further include an image capture device that captures the image that depicts at least the specimen validity portion of the specimen test article, the image capture device communicatively coupled to the at least one processor. To assess at least one specimen validity characteristic, the processor may determine the validity of the specimen based at least in part on each color component value of the determined set of color component values. To assess at least one specimen validity characteristic, the processor may select one of a plurality of potential values of a physical characteristic of the specimen based at least in part on each color component value of the determined set of color component values.

Execution of the at least one of the processor-executable instructions or data may further cause the at least one processor to: determine the validity of the specimen based at least in part on the selected one of the plurality of potential values of the physical characteristic of the specimen. The physical characteristic of the specimen may include one or more of a pH of the specimen and a specific gravity of the specimen.

The at least one non-transitory processor-readable medium may further store at least one lookup table and to assess at least one specimen validity characteristic, the processor uses the lookup table to select a value of the at least one specimen validity characteristic based at least in part on each color component value of the set of color component values.

The set of color component values may include at least a first color component value, a second color component value, and a third color component value, the at least one non-transitory processor-readable medium may further store a plurality of sets of reference color component values, each set of reference color component values comprising at least a first reference color component value, a second reference color component value, and a third reference color component value, and to assess at least one specimen validity characteristic, the processor identifies a first set of reference color component values of the plurality of sets of reference color component values that is closest to the set of color component values determined for the one or more of the plurality of pixels.

To assess at least one specimen validity characteristic, the processor may further assess the at least one specimen validity characteristic based at least in part on the identified first set of reference color component values. To identify a first set of reference color component values, the processor may determine a distance value for each of the plurality of sets of reference color component values and select the set of reference color component values with the smallest distance value as the first set of reference color component values. To determine a distance value for each of the plurality of sets of reference color component values, the processor respectively may input each of the plurality of sets of reference color component values into a distance formula with the set of color component values to determine the distance value for such set of reference color component values, the distance formula including a square root of a first squared difference between the first color component value and the first reference color component value of the inputted set of reference color component values plus a second squared difference between the second color component value and the second reference color component value of the inputted set of reference color component values plus a third squared difference between the third color component value and the third reference color component value of the inputted set of reference color component values.

To assess at least one specimen validity characteristic, the processor may further select a value of a physical characteristic of the specimen associated with the first set of reference color component values and execution of the at least one of the processor-executable instructions or data may further cause the at least one processor to determine the validity of the specimen based at least in part on the selected value of the physical characteristic. To determine the validity of the specimen, the processor may select a specimen validity status associated with the selected value of the physical characteristic in a lookup table.

A computer-implemented method to analyze specimen test articles which include at least one optical test subject substance marker that indicates at least a presence or an absence of a test subject substance in a specimen, and at least one optical specimen validity marker, a color of which indicates a validity of the specimen may be summarized as including receiving, by one or more computing devices, a set of image information that represents an image of at least a specimen validity portion of the specimen test article which includes the at least one optical specimen validity marker, the color of which indicates the validity of the specimen; determining, by the one or more computing devices, a set of color component values for one or more of a plurality of pixels of the image that are representative of the specimen validity portion of the specimen test article, the set of color component values comprising at least three color component values, each of the color component values representative of an amount of a respective color component of a color of the corresponding one or more of the plurality of pixels of the image; and assessing, by the one or more computing devices, at least one specimen validity characteristic of the specimen based at least in part on each color component value of the determined set of color component values for the one or more of the plurality of pixels of the image. Determining a set of color component values may include determining, by the one or more computing devices, a red color component value, a green color component value, and a blue color component value. Assessing at least one specimen validity characteristic may include assessing, by the one or more computing devices, the at least one specimen validity characteristic based at least in part on each of a red color component value, a green color component value, and a blue color component value. Assessing at least one specimen validity characteristic may include assessing, by the one or more computing devices, at least a first specimen validity characteristic based at least in part on each of a first red color component value, a first green color component value, and a first blue color component value of a first one of the at least one optical specimen validity marker, and assessing, by the one or more computing devices, at least a second specimen validity characteristic based at least in part on each of a second red color component value, a second green color component value, and the second blue color component value of a second one of the at least one optical specimen validity marker. Assessing at least one specimen validity characteristic may include assessing, by the one or more computing devices, the presence or the absence of one or more of oxidants, creatinine, nitrite, and aldehydes in the specimen.

The computer-implemented method may further include assessing, by the one or more computing devices, the presence or the absence of the test subject substance in the specimen based at least in part on the at least one optical test subject substance marker. Assessing the presence or absence of the test subject substance may include assessing, by the one or more computing devices, the presence or absence of one or more of alcohol, cocaine, marijuana, amphetamines, performance enhancing drugs, substances indicative of use of alcohol, cocaine, marijuana, amphetamines, or performance enhancing drugs, or derivatives of alcohol, cocaine, marijuana, amphetamines, or performance enhancing drugs in the specimen. Receiving the set of image information may include receiving, by the one or more computing devices, the set of image information that represents the image of at least the specimen validity portion of a lateral flow strip, and the at least one optical test subject substance marker that indicates at least the presence or the absence of the test subject substance in the specimen is spaced on the lateral flow strip from the at least one optical specimen validity marker, the color which indicates the validity of the specimen.

The computer-implemented method may further include capturing, by an image capture device, the image that depicts at least the specimen validity portion of the specimen test article. Assessing at least one specimen validity characteristic may include determining, by the one or more computing devices, the validity of the specimen based at least in part on each color component value of the determined set of color component values. Assessing at least one specimen validity characteristic may include selecting, by the one or more computing devices, one of a plurality of potential values of a physical characteristic of the specimen based at least in part on each color component value of the determined set of color component values.

The computer-implemented method may further include determining, by the one or more computing devices, the validity of the specimen based at least in part on the selected one of the plurality of potential values of the physical characteristic of the specimen. Selecting one of a plurality of potential values of a physical characteristic of the specimen may include selecting, by the one or more computing devices, one of a plurality of potential pH values of the specimen or selecting, by the one or more computing devices one of a plurality of potential specific gravity values of the specimen. Assessing at least one specimen validity characteristic may include using, by the one or more computing devices, a lookup table to select a value of the at least one specimen validity characteristic based at least in part on each color component value of the determined set of color component values. Determining a set of color component values may include determining, by the one or more computing devices, at least a first color component value, a second color component value, and a third color component value, and assessing at least one specimen validity characteristic comprises identifying, by the one or more computing devices, a first set of reference color component values from a plurality of sets of reference color component values that is closest to the set of color component values determined for the one or more of the plurality of pixels, each set of reference color component values including at least a first reference color component value, a second reference color component value, and a third reference color component value.

Assessing the at least one specimen validity characteristic may further include assessing, by the one or more computing devices, the at least one specimen validity characteristic based at least in part on the identified first set of reference color component values. Identifying a first set of reference color component values may include determining, by the one or more computing devices, a distance value for each of the plurality of sets of reference color component values and selecting, by the one or more computing devices, the set of reference color component values with the smallest distance value as the first set of reference color component values. Determining a distance value may include respectively inputting, by the one or more computing devices, each of the plurality of sets of reference color component values into a distance formula with the set of color component values to determine the distance value for such set of reference color component values, the distance formula comprising a square root of a first squared difference between the first color component value and the first reference color component value of the inputted set of reference color component values plus a second squared difference between the second color component value and the second reference color component value of the inputted set of reference color component values plus a third squared difference between the third color component value and the third reference color component value of the inputted set of reference color component values.

Assessing the at least one specimen validity characteristic may further include selecting, by the one or more computing devices a value of a physical characteristic of the specimen associated with the first set of reference color component values and determining, by the one or more computing devices, the validity of the specimen based at least in part on the selected value of physical characteristic.

Determining the validity of the specimen may include selecting, by the one or more computing devices, a specimen validity status associated with the selected value of the physical characteristic a lookup table.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not necessarily drawn to scale, and some of these elements may be arbitrarily enlarged and positioned to improve drawing legibility. Further, the particular shapes of the elements as drawn, are not necessarily intended to convey any information regarding the actual shape of the particular elements, and may have been solely selected for ease of recognition in the drawings.

FIG. 4 is an example lookup table, according to at least one illustrated embodiment.

FIG. 5 is an example lookup table, according to at least one illustrated embodiment.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures and methods (e.g., various components of computing devices, principles of operation of a lateral flow strip, etc.) have not been shown or described in detail to avoid unnecessarily obscuring descriptions of the embodiments.

Unless the context requires otherwise, throughout the specification and claims that follow, the word "comprising" is synonymous with "including," and is inclusive or open-ended (i.e., does not exclude additional, unrecited elements or method acts).

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the context clearly dictates otherwise. It should also be noted that the term "or" is generally employed in its broadest sense, that is, as meaning "and/or" unless the context clearly dictates otherwise.

The headings and Abstract of the Disclosure provided herein are for convenience only and do not interpret the scope or meaning of the embodiments.

Figure 1:
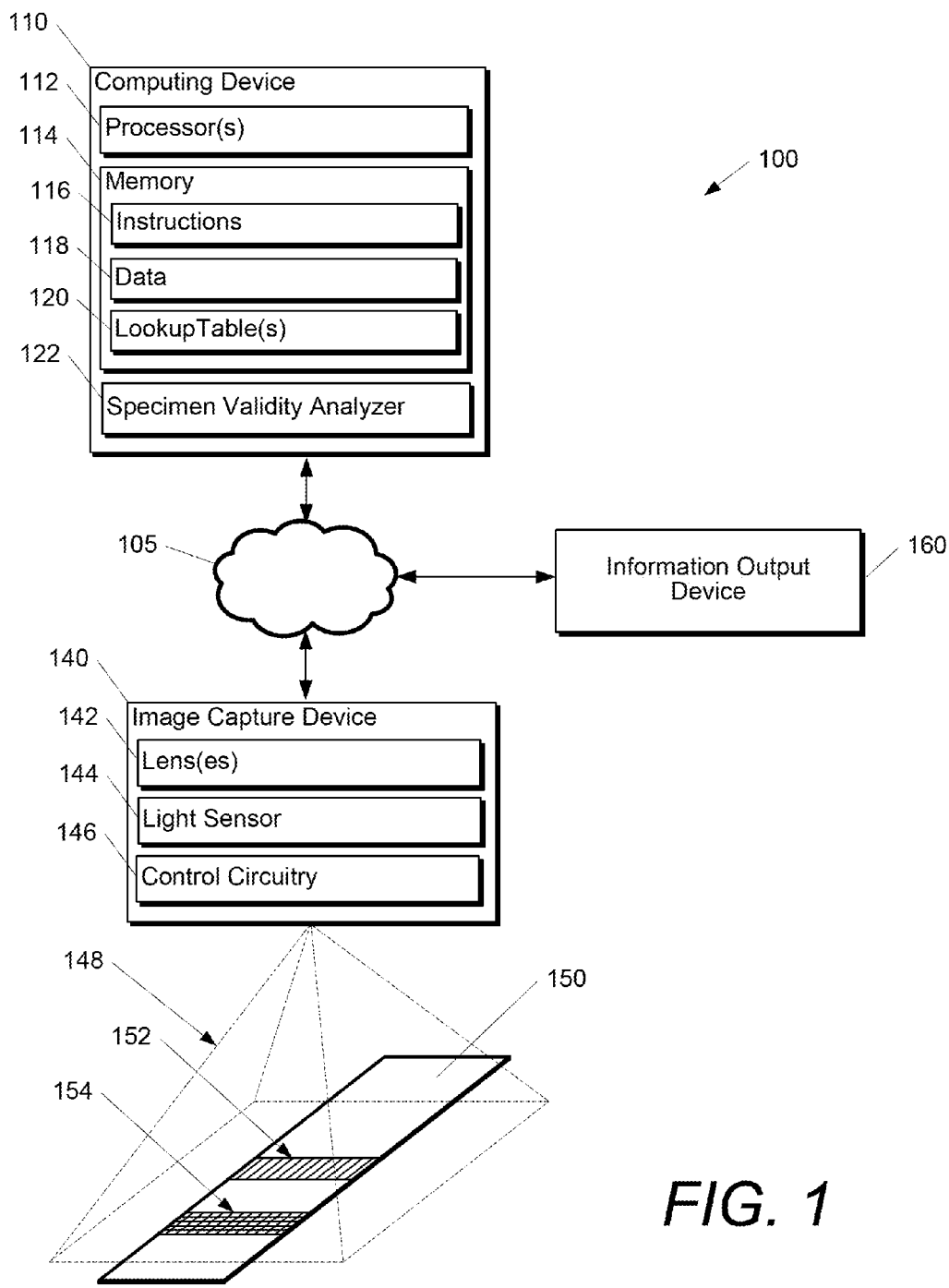
FIG. 1 is block diagram of an example specimen analysis system, according to at least one illustrated embodiment.

FIG. 1 is block diagram of an example specimen analysis system 100, according to at least one illustrated embodiment. The system 100 includes a computing device 110, an image capture device 140, and an information output device 160 communicatively coupled directly or over a network 105. The system 100 analyzes specimen test articles, such as a specimen test article 150 shown in FIG. 1. In some implementations, a single housing or assembly encloses the computing device 110, the image capture device 140, and information output device 160.

The specimen test article 150 is used to test for the presence or absence of a test subject substance in a specimen. As examples, the specimen test article 150 can test a specimen for the presence or absence of alcohol, cocaine, marijuana (THC), amphetamines, performance enhancing drugs, other banned substances, other test subject substances indicative of use of a particular substance, or combinations and/or derivatives thereof. As examples, the specimen can take the form of human or animal urine, blood, saliva, semen, or other bodily fluids or bodily matter.

The specimen test article 150 includes at least one optical test substance marker 152. The optical test substance marker 152 indicates at least the presence or the absence of the test subject substance in the specimen. For example, a color of the optical test substance marker 152 indicates the presence or absence of the test subject substance in the specimen. As one example, the color of the optical test substance marker 152 remains unchanged from a first color if the specimen does not contain the test subject substance, while the color of the optical test substance marker 152 changes from the first color to a second, different color if the test subject substance is present within the specimen.

In some implementations, presence of the test subject substance within the specimen may be defined as an amount or concentration of the test substance that is greater than a threshold value. Furthermore, in some implementations, the color of the optical test substance marker 152 changes along a spectrum or among a plurality of colors to indicate an amount or a concentration of the test subject substance within the specimen.

The specimen test article 150 also includes at least one optical specimen validity marker 154 in addition to the optical test substance marker 152. In some implementations, the optical specimen validity marker 154 is spaced from the optical test substance marker 152 (e.g., such that the two markers 154 and 152 are readily distinguishable from each other).

A color of the optical specimen validity marker 154 indicates a validity of the specimen. Thus, in contrast to the test subject substance for which the specimen is principally being tested, the specimen validity maker 154 provides an indication of whether or not the specimen itself is valid or authentic, and/or unadulterated or untampered. As an example, where the optical test substance maker 152 may indicate the presence or absence of cocaine within the specimen, the specimen validity maker 154 may indicate whether the specimen itself is human urine.

As one example method of operation, the optical specimen validity marker 154 changes colors in the presence of an adulterant, where the presence of an adulterant renders the specimen invalid. As another example, the optical specimen validity marker 154 may remain the same color in the absence of a particular substance in the specimen, where the absence of the particular substance in the specimen renders the specimen invalid.

As yet another example, the color of the optical specimen validity marker 154 may indicate a value or status of a physical characteristic of the specimen. The validity of the specimen is then inferable or otherwise determinable from the indicated value or status of the physical characteristic. As examples, the physical characteristic can include a pH of the specimen, a specific gravity of the specimen, a salinity of the specimen, a temperature of the specimen, or other physical characteristics or combinations of characteristics.

Thus, the optical specimen validity marker 154 may assess specimen validity according to many different methods of operation, including detection of an adulterant within the specimen, absence of a substance expected to be found in unadulterated specimens, specimen physical characteristics, or other techniques or combinations thereof.

As one example, if the optical specimen validity marker 154 indicates that the temperature of a specimen (e.g., human urine specimen) is less than a threshold temperature, the specimen may be ruled invalid. Such may advantageously detect submission by the donor of a specimen not produced within a designated testing area or testing period.

As a further example, the optical specimen validity marker 154 may test for the presence of acidic and/or alkaline adulterants within a human urine specimen. In particular, the color of the optical specimen validity marker 154 may indicate a pH of the specimen. Human urine typically has pH values that range from 4.0 to 9.0. Therefore, if the color of specimen validity marker 154 indicates that the specimen has a pH below 4.0 or above 9.0, the specimen may be ruled invalid.

As another example, the optical specimen validity marker 154 may test for dilution of a human urine specimen. In particular, the color of the optical specimen validity marker 154 may indicate a specific gravity of the specimen. Human urine typically has specific gravity values that range from 1.003 to 1.030. Therefore, if the color of specimen validity marker 154 indicates that the specimen has a specific gravity below 1.003 or above 1.030, the specimen may be ruled invalid.

As another example, the optical specimen validity marker 154 may test for the presence of oxidants, such as bleach or peroxide, within a human urine specimen. In particular, the optical specimen validity marker 154 may turn a blue or green color in the presence of oxidants. Therefore, if the specimen validity marker 154 is the blue or green color, the specimen may be ruled invalid.

As another example, the optical specimen validity marker 154 may test for dilution of a human urine specimen by indicating the presence or absence of creatinine, which is a waste product of creatine and is typically present in human urine. In particular, the color of the optical specimen validity marker 154 may indicate the presence or absence of creatinine. For example, a donor may attempt to alter a test by consuming excessive amounts of water or diuretics to "flush" his or her urinary system. Therefore, if the color of the specimen validity marker 154 indicates an absence of creatinine within the specimen (e.g., less than 5 mg/dl), the specimen may be ruled invalid.

As another example, the color of the optical specimen validity marker 154 may indicate the presence or absence of nitrites a human urine specimen. In particular, nitrites are contained within many commercially available urine adulterants and work by oxidizing a major cannabinoid metabolite THC-COOH. Unadulterated urine does not normally contain any nitrites. Therefore, if the color of the specimen validity maker 154 indicates the presence of nitrites within the specimen, the specimen may be ruled invalid.

As yet another example, the color of the optical specimen validity maker 154 may indicate the presence of one or more aldehydes such as glutaraldehyde within a human urine specimen. In particular, glutaraldehyde is contained within many commercially available urine adulterants and causes false negative screening results by disrupting an enzyme used in some specimen test articles 150. Unadulterated urine does not normally contain any aldehydes. Therefore, if the color of the specimen validity maker 154 indicates the presence of aldehydes within the specimen, the specimen may be ruled invalid.

In some implementations, presence or absence of a particular substance (e.g., an adulterant) within the specimen may be defined as an amount or concentration of the substance that is greater than or less than a threshold value. Furthermore, in some implementations, the color of the optical specimen validity maker 154 changes along a spectrum or among a plurality of colors to indicate an amount or a concentration of a particular substance within the specimen or to indicate a range of potential values of a physical characteristic of the specimen. For example, the optical specimen validity marker 154 may increasingly change from a first color to a second color to indicate the pH of the specimen within a range of potential pH values or may increasingly change from the first color to the second color to indicate a concentration of, for example, aldehydes within the specimen.

In some implementations, the specimen test article 150 includes two or more specimen validity markers 154 which operate to assess specimen validity according to different methods. In some of such implementations, if any of the two or more markers 154 indicate that the specimen is invalid, then the specimen may be ruled invalid. In others of such implementations, if greater than or equal to some predetermined number of the two or more markers 154 (e.g., two, three, all, etc.) indicate that the specimen is invalid, then the specimen may be ruled invalid.

In some implementations, the specimen test article 150 additionally includes a control marker (not shown) that simply indicates whether the specimen test article properly absorbed or otherwise received the specimen. Further, in some implementations, the specimen test article 150 includes only the optical specimen validity marker 154 and not the optical test substance marker 152. In some implementations, the specimen test article 150 is a lateral flow strip.

In addition, although certain of the example test subject substances discussed above are illicit or banned substances, the present disclosure is not limited to testing for such category of substances. Instead, the systems and methods of the present disclosure can be used with any specimen test article 150 that includes an optical specimen validity marker 154 that indicates with its color a validity characteristic of the specimen. As an example, the specimen analysis system 100 can be used to assess a validity characteristic of a specimen that is tested for one or more substances indicative of various illnesses, diseases, genetic traits, or other medically pertinent information. Therefore, the specimen analysis system 100 may be used in conjunction with or as a portion of a diagnostic protocol. For example, the specimen test article 150 may be a diagnostic assay.

The image capture device 140 can be any device capable of capturing an image. For example, the image capture device 140 can be one or more of many different types of cameras, scanners, or other devices capable of capturing an image or image data.

As an example, the image capture device 140 includes a number of lenses 142 that modify, redirect, and/or focus light entering the image capture device 140 through an aperture. A light sensor 144 receives the light that passes through the lenses 142 and outputs data representative of a plurality of pixels of an image. For example, the light sensor 144 can output data representative of a color for each of the plurality of pixels, as discussed further below.

The image capture device 140 also includes control circuitry 146 that controls operation of the image capture device 140. For example, the control circuitry 146 controls image capture timing, image capture rate, image resolution, or other parameters of image capture device 140. In some implementations, the computing device 110 controls or provides instructions to the image capture device 140 directly or via network 105.

The image capture device 140 captures an image of a field of view 148 of the image capture device 140. As shown in FIG. 1, the specimen test article 150 is positioned relative to the image capture device 140 such that at least a specimen validity portion of the specimen test article which includes the at least one optical specimen validity marker 154 is included within the field of view 148 and corresponding captured image. The at least one optical test substance marker 152 may be included within the field of view 148 and corresponding captured image, as shown in FIG. 1, or may not be included within the field of view 148 and corresponding captured image.

In some implementations, the image capture device 140 includes a structure or device that receives the specimen test article 150 and positions the specimen validity portion of the test article 150 within the field of view 148. As one example, a cartridge that is insertable into the image capture device 140 or an associated structure receives and holds the specimen test article 150. Alternatively or additionally, system 100 may include other means for placing the specimen test article 150 in a known position and/or orientation relative to the image capture device 140. Such may advantageously allow the captured image to depict only the optical specimen validity marker 154 or otherwise allow simplified identification and/or isolation of the pixels of the captured image that corresponds to the optical specimen validity marker 154.

In further implementations, the image capture device includes one or more internal or external light sources to illuminate the specimen test article 150 during image capture. For example, the light source(s) can include one or more light emitting diodes, lamps, incandescent bulbs, infrared light sources, light sources for inducing fluorescence from the article 150 (e.g., from marker 152 and/or marker 154), or other light sources.

The image capture device 140 outputs or otherwise provides to the computing device 110 directly or over network 105 a set of image information that represents the captured image of at least the specimen validity portion of the specimen test article 150. For example, the set of image information includes data representative of a plurality of pixels of the image. In particular, the data includes three or more color component values for each of the plurality of pixels. Each of the color component values is representative of an amount of a respective color component of a color of the corresponding pixel.

As one example, the color component values for each pixel include a red color component value, a green color component value, and a blue color component value, thereby describing the color of such pixel within the RGB color space. For example, each of such values may range from 0 to 255. However, other color component value ranges may be used.

In other implementations, alternatively or in addition to the RGB color space, the color component values included in the set of image information can describe colors of pixels according to the RGBA color space, CMYK color space, YIQ color space, YPbPr color space, xvYCC color space, HSV color space, HSL color space, or other color spaces or color models, or combinations thereof. The computing device 110 uses the color component values to assess the optical specimen validity maker 154, as discussed further below.

The computing device 110 can be an embedded computing device, a desktop computer, a laptop computer, a tablet computer, a smartphone, one or more server computing devices, or some combination thereof. The computing device 110 can perform computing operations according to any computer architecture, including parallel, sequential, and/or distributed computing architectures.

Computing device 110 includes a processor 112 and a memory 114. The processor 112 can be one processor or a plurality of processors that are operatively coupled. The processor 112 can be any processing device, such as a microprocessor, microcontroller, integrated circuit, circuitry that implements computer logic, or some combination thereof.

The memory 114 can include any non-transitory information storage device, including, but not limited to, RAM, ROM, hard drives, flash drives, optical media, other memory devices, or some combination thereof. The memory 114 can store information accessible by processor 112, including instructions 116 that can be executed by processor 112. The instructions 116 can be any set of instructions that when executed by the processor 112, cause the processor 112 to provide desired functionality. The memory 114 can also store data 118.

The computing device 110 includes a specimen validity analyzer 122. The computing device 110 implements the specimen validity analyzer 122 to assess at least one specimen validity characteristic of the specimen. In some implementations, the specimen validity analyzer 122 assesses the at least one specimen validity characteristic based at least in part on a set of color component values determined for one or more pixels of the image of the specimen test article 150. For example, computing device 110 can implement specimen validity analyzer 122 to perform aspects of methods 200 and 300 of FIGS. 2 and 3, respectively, as discussed further below.

In some implementations, the specimen validity analyzer 122 includes processor-executable instructions 116 stored in or loaded into memory 114 and executed by processor 112. In other implementations, the specimen validity analyzer 122 includes one or more circuits (e.g., integrated circuits), logic components, or other items of computer hardware arranged to implement computer logic or perform other functionality. In other implementations, the specimen validity analyzer 122 can be implemented using some combination of processor-executable instructions 116 or data 118 and circuitry.

In some implementations, the memory 114 also stores one or more lookup tables 120. Each lookup table 120 stores information usable in association with one or more particular varieties of specimen test articles 150. For example, each different variety of specimen test article 150 may test for a different test substance or may test specimen validity according to a different respective methods of operation.

The lookup table 120 for each particular variety of specimen test article 150 provides a mapping of potential colors of specimen validity marker 154 to particular respective test results indicated by such colors. More precisely, the lookup table for each particular variety of specimen test article 150 logically associates each of a plurality of sets of reference color component values with a particular result or value of at least one specimen validity characteristic. The same or additional lookup tables can provide analogous information for marker 152.

As an example, FIG. 4 is an example lookup table 400, according to at least one illustrated embodiment. Lookup table 400 includes a plurality of sets of reference color component values in a first column 402 and a plurality of specimen validity characteristic results or values in a second column 404. Each set of reference color component values (e.g., sets 410, 412, and 414) is respectively logically associated with a particular specimen validity characteristic result (e.g., validity characteristic results 420, 422, and 424).

Referring again to FIG. 1, in some implementations, the lookup table 120 for a particular specimen test article 150 logically associates each set of reference color component values with a particular value of a physical characteristic of the specimen. In some implementations, the lookup table 120 further logically associates each set of reference color component values and/or each particular value of the physical characteristic with a particular specimen validity status.

As an example, FIG. 5 is an example lookup table 500, according to at least one illustrated embodiment. Lookup table 500 includes a plurality of sets of reference color component values in a first column 502; a plurality of specimen physical characteristic values in a second column 504; and a plurality of specimen validity status results or values in a third column 506. Each set of reference color component values (e.g., sets 510, 512, 514, and 516) is respectively logically associated with a particular specimen physical characteristic value (e.g., physical characteristic values 520, 522, 524, and 526). Furthermore, each set of reference color component values and/or each physical characteristic value is respectively logically associated with a particular specimen validity status (e.g., statuses 530, 532, 534, and 536).

Referring again to FIG. 1, in some implementations, the specimen validity analyzer 122 uses the lookup tables 120 to assess at least one specimen validity characteristic of the specimen. For example, the specimen validity analyzer 122 may use the lookup tables 120 to map a set of color component values representative of a color of the specimen validity marker 154 to a particular specimen validity characteristic outcome, as discussed further below with respect to methods 200 and 300 of FIGS. 2 and 3, respectively.

Generally, the information stored within each lookup table 120 (e.g., sets of reference color component values, specimen validity characteristic values, physical characteristic values, and/or specimen validity statuses) and their associated relationships are predetermined through testing or calibration of the corresponding variety of specimen test article 150 with reference specimen samples having known validity or physical characteristic values.

As one example, a particular variety of specimen test articles 150 may test for the presence of acidic and/or alkaline adulterants within human urine by indicating specimen pH, as discussed above. The pH values of unadulterated human urine typically range from 4.0 to 9.0. Therefore, pH values below 4.0 or above 9.0 for a specimen are indicative of adulteration. As such, to generate the lookup table 120 for such particular variety of specimen test articles 150, reference specimen samples having known pH values may be respectively placed on different specimen test articles 150 of such variety. The resulting color of the optical specimen validity marker 154 of each respective specimen test article 150 may be determined (e.g., in the form of sets of reference color component values) and logically associated with the known pH of the reference specimen sample to which such test article 150 was subjected.

In some implementations, an operator of the system 100 performs such example calibration or testing process to obtain the information and relationships stored in the lookup tables 120. In other implementations, a manufacturer of a particular variety of specimen test articles 150 provides the lookup table 120 or the information stored within the lookup table 120 (e.g., in the form of a computer-readable file or in the form of a textual description that an operator of the system 100 inputs into the computing device 110).

Furthermore, the respective structures of the example lookup tables 400 and 500 of FIGS. 4 and 5 are provided as examples only. Lookup tables 120 may have other, different structures, as well.

The particular reference color component values or physical characteristic values contained within a lookup table 120 may be spaced along uniform intervals or may be spaced along non-uniform intervals. For example, in some implementations, the reference color component values or physical characteristic values included in a lookup table 120 may be particularly grouped around values that correspond to transitions between valid and invalid specimens. To continue the example provided above, a lookup table 120 for specimen test articles 150 that test for the presence of acidic and/or alkaline adulterants within human urine via specimen pH value may include relatively greater numbers of sets of reference color component that respectively correspond to pH values grouped around pH 4.0 and pH 9.0, thereby providing increased testing granularity around the transitions between valid and invalid human urine specimens.

System 100 further includes the information output device 160. The information output device 160 provides information regarding at least one specimen validity characteristic of the specimen that has been assessed by the system 100 to a user. For example, the information output device 160 can be any display device to present or show the information, including, for example, a monitor, a screen, a holographic display, a projection display, a three-dimensional display, etc.

As another example, the information output device 160 can include a plurality of light emitting diodes, with each of the light emitting diodes corresponding to a different value or outcome of the at least one specimen validity characteristic. The system 100 can illuminate one or more light emitting diodes to convey information regarding the assessed specimen validity characteristic.

As yet another example, the information output device 160 can include a printer to print information, a speaker to audibly output information, and/or a network interface to transmit information regarding the assessed specimen validity characteristic to one or more remote devices or systems via network 105.

Network 105 can be any type of communications network, such as a local area network (e.g., intranet), a wide area network (e.g., Internet), or some combination thereof and can include any number of wired or wireless links. In general, communication between the components of system 100 via network 105 can be carried via any type of wired and/or wireless connection, using a wide variety of communication protocols (e.g., TCP/IP, HTTP, SMTP, FTP), encodings or formats (e.g., HTML, XML), and/or protection schemes (e.g., VPN, secure HTTP, SSL). Thus, communications over network 105 can include direct, wired communication, wireless communications, or combinations thereof. For example, network 105 can include a direct, wired communicative connection (e.g., wired USB connection) between computing device 110 and image capture device 140.

Figure 2:
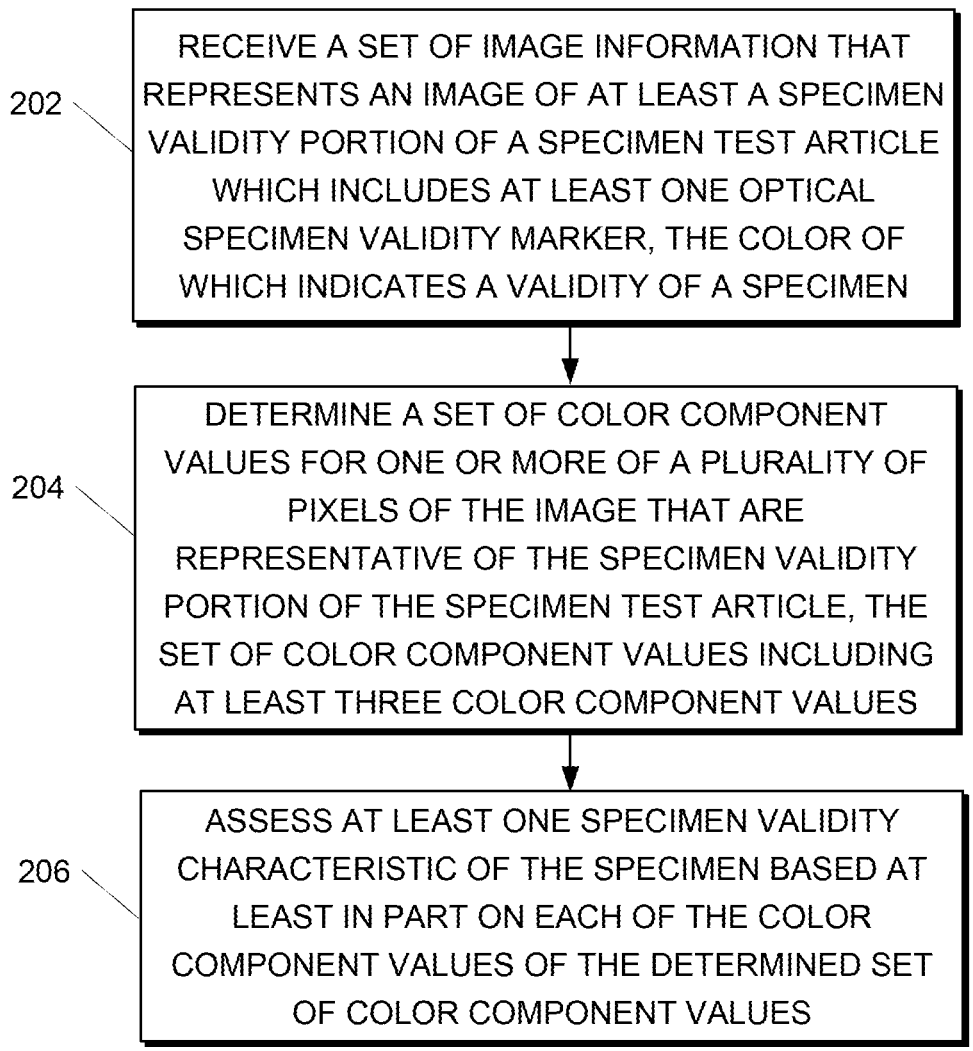
FIG. 2 is a flow chart diagram showing an example method to analyze specimen test articles, according to at least one illustrated embodiment.

FIG. 2 is a flow chart diagram showing an example method 200 to analyze specimen test articles, according to at least one illustrated embodiment. Although method 200 is discussed herein with reference to the specimen validity analyzer 122 of FIG. 1, any suitable specimen analysis system can perform method 200. Likewise, certain portions of method 200 may be performed by other components of system 100 alternatively or in addition to the specimen validity analyzer 122. Method 200 begins at 202.

At 202, the specimen validity analyzer 122 receives a set of image information that represents an image of at least a specimen validity portion of a specimen test article. The specimen validity portion of the test article includes the at least one optical specimen validity marker, the color of which indicates a validity of the specimen. For example, the specimen validity analyzer 122 can receive a set of image information from the image capture device 140 that represents a captured image of the specimen test article 150 which includes the optical specimen validity marker 154.

In some implementations, the set of image information describes a plurality of pixels of the image. In particular, the set of image information can include, for each of the plurality of pixels, at least three color component values that describe the color of such pixel. Each of the color component values can represent an amount of a color component of the color of the corresponding pixel. For example, the color component values can describe colors according to according the RGB color space, RGBA color space, CMYK color space, YIQ color space, YPbPr color space, xvYCC color space, HSV color space, HSL color space, or other color spaces or color models, or combinations thereof.

At 204, the specimen validity analyzer 122 determines a set of color component values for one or more of a plurality of pixels of the image that are representative of the specimen validity portion of the specimen test article. The set of color component values includes at least three color component values.

In some implementations, the specimen validity analyzer 122 determines the set of color component values at 204 by performing one or more preprocessing routines or operations to isolate or otherwise identify the image data that corresponds to pixels of the captured image that are representative of the optical specimen validity marker 154.

As an example, in some implementations, the specimen test article 150 includes an additional optically identifiable marker or symbol that indicates a known direction, has a known size, and/or has a known position relative to the optical specimen validity marker 154. The specimen validity analyzer 122 identifies the additional symbol; computes or otherwise determines the location and size of the optical specimen validity marker 154 within the image based on the size, direction, and/or position of the additional symbol; and isolates or otherwise identifies the image data that corresponds to pixels of the captured image that are representative of the optical specimen validity marker 154. In some implementations, the additional symbol is included or located within the optical specimen validity marker 154.

As another example, in some implementations, the specimen validity analyzer 122 identifies or determines an outline or perimeter of the specimen test article 150; computes or otherwise determines the location and size of the optical specimen validity marker 154 within the image based on the perimeter of the specimen test article 150; and isolates or otherwise identifies the image data that corresponds to pixels of the captured image that are representative of the optical specimen validity marker 154. In other implementations, the specimen validity analyzer 122 directly identifies an outline or perimeter of the optical specimen validity marker 154. In yet other implementations, the specimen validity analyzer 122 performs other, different preprocessing operations in addition or alternatively to the above described operations.

In some implementations, the specimen validity analyzer 122 determines the set of color component values for the one or more pixels representative of the specimen validity portion of the specimen test article at 204 by calculating a set of average color component values (e.g. mean or median)

across all of such pixels. In further implementations, the specimen validity analyzer can identify and disregard pixels having outlying color component values.

Thus, at 204, the specimen validity analyzer determines a set of at least three color component values for one or more pixels representative of the specimen validity portion of the test article 150. For example, the set of determined color component values can include a red color component value, a blue color component value, and a green color component value.

At 206, the specimen validity analyzer 122 assesses at least one specimen validity characteristic of the specimen based at least in part on each of the color component values of the set of color component values determined at 204. As an example, the specimen validity analyzer 122 can assess the validity of the specimen based at least in part on each of the color component values determined at 204. As another example, the specimen validity analyzer 122 can determine a value of a physical characteristic of the specimen based at least in part on each of the color component values determined at 204. In some implementations, the specimen validity analyzer 122 further assesses the validity of the specimen based at least in part on the determined value of the physical characteristic.

Figure 3:
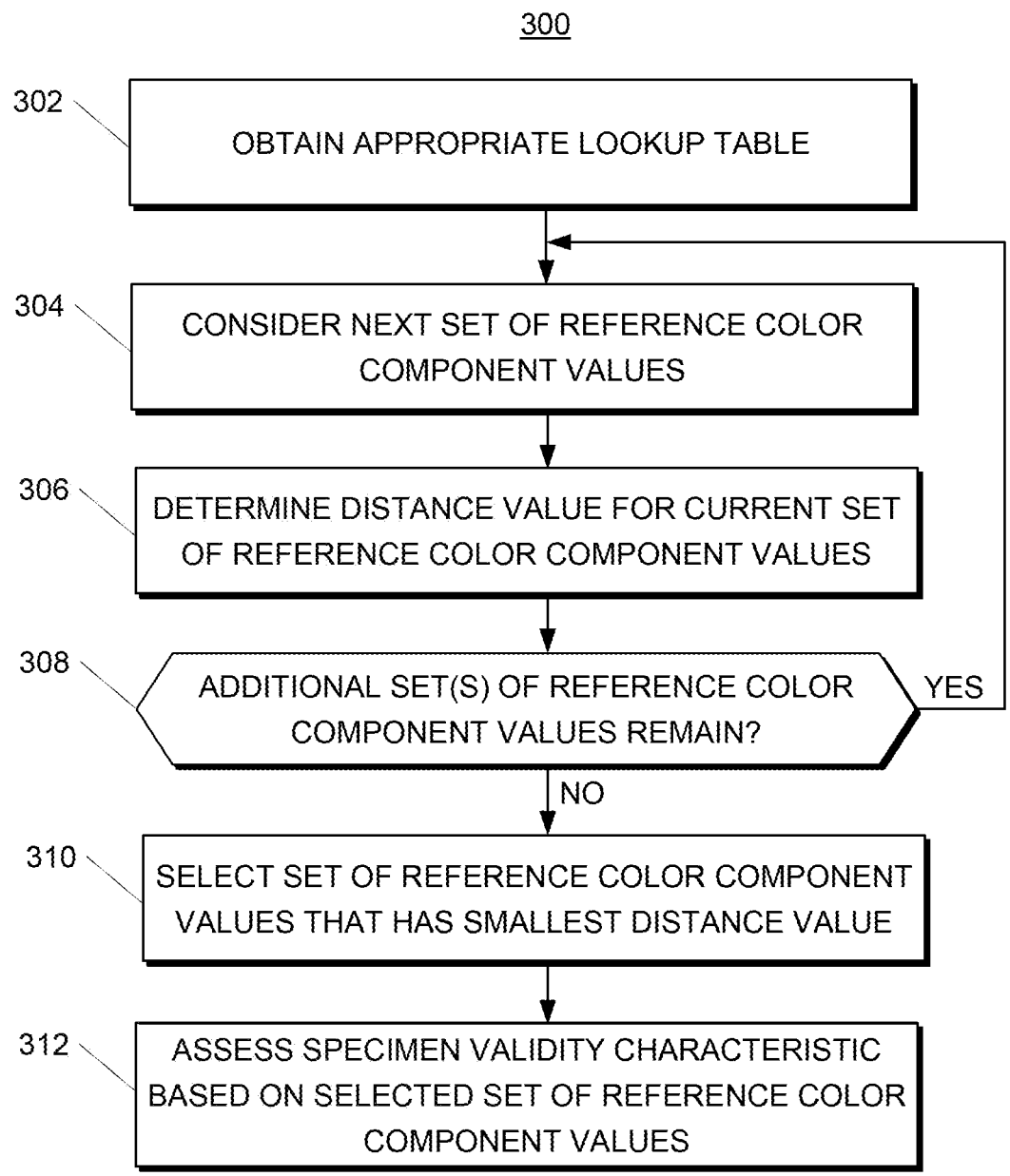
FIG. 3 is a flow chart diagram showing an example method to assess at least one specimen validity characteristic, according to at least one illustrated embodiment.

As one example, FIG. 3 is a flow chart diagram showing an example method 300 to assess at least one specimen validity characteristic, according to at least one illustrated embodiment. Although method 300 is discussed herein with reference to the specimen validity analyzer 122 of FIG. 1, any suitable specimen analysis system can perform method 300. Likewise, certain portions of method 300 may be performed by other components of system 100 alternatively or in addition to the specimen validity analyzer 122. Method 300 begins at 302.

At 302, the specimen validity analyzer 122 obtains an appropriate lookup table. For example, in some implementations, the computing device 110 stores a plurality of lookup tables 120 in memory 114. Each lookup table 120 is associated with a particular variety of specimen test articles 150. For example, a particular variety of specimen test article 150 may test for a particular test substance and/or test and indicate specimen validity according to particular respective methods of operation.

The lookup table 120 associated with each particular variety of specimen test article 150 includes, for example, a set of reference color component values respectively logically associated with a plurality of specimen validity characteristic values or results. Thus, to assess the at least one specimen validity characteristic, the specimen validity analyzer 122 first obtains the particular lookup table 120 that is appropriate for the particular specimen test article 150 being analyzed.

As an example, in some implementations, the specimen test article 150 includes a machine-readable symbol or textual, numeric, or graphical information that identifies the specimen test article 150 or its particular variety. The specimen validity analyzer 122 uses such symbol or information to identify the specimen test article 150 or its particular variety. The specimen validity analyzer 122 then obtains the particular lookup table 120 that is appropriate for the identified variety of specimen test article 150 from memory 114.

In other implementations, the specimen validity analyzer 122 obtains the identity or particular variety of the specimen test article 150 or the identity of the appropriate lookup table 120 via user input.

At 304, the specimen validity analyzer 122 considers the next set of reference color component values. More particularly, the lookup table obtained at 302 includes a plurality of sets of reference color component values. Thus, at 304, the specimen validity analyzer 122 considers the next set of reference color component values. In such fashion, each set of reference color component values is considered individually. Although method 300 shows the specimen validity analyzer considering the sets of reference color component values sequentially, in some implementations, the specimen validity analyzer 122 considers the sets of reference color component values in parallel.

At 306, the specimen validity analyzer 122 determines a distance value for the currently considered set of reference color component values. For example, the specimen validity analyzer 122 inputs the currently considered set of reference color component values into a distance formula to determine the distance value for the current set of reference color component values. The distance formula compares the currently considered set of reference color component values to the set of color component values determined for the one or more pixels to provide the distance value for the current set of reference color component values. In particular, the distance value provided by the distance formula can indicate a "closeness" between the two inputted sets of color component values.

As an example, in some implementations, the specimen validity analyzer 122 uses the following example distance formula to determine the distance value at 306:

$$D = \sqrt{(Test_1 - Ref_1)^2 + (Test_2 - Ref_2)^2 + \ldots + (Test_N - Ref_N)^2} \quad (1)$$

where D is the distance value; $Test_x$ is a member of the set of color component values determined for the one or more pixels representative of the specimen validity portion of the test article; and $Ref_x$ is a member of the currently considered set of reference color component values.

At 308, the specimen validity analyzer 122 determines whether additional sets of reference color component values from the lookup table remain unconsidered. If the specimen validity analyzer 122 determines at 308 that one or more additional sets of reference color component values remain, the specimen validity analyzer 122 returns to 304 and considers the next set of reference color component values.

However, if specimen validity analyzer 122 determines at 308 that no additional sets of reference color component values remain, then specimen validity analyzer 122 proceeds to 310. At 310, the specimen validity analyzer 122 selects the set of reference color component values that has the smallest distance value.

At 312, the specimen validity analyzer 122 assesses at least one specimen validity characteristic based at least in part on the set of reference color component values selected at 310. For example, the specimen validity analyzer 122 may select a specimen validity characteristic value or result that is logically associated with the set of reference color component values selected at 310 in the lookup table obtained at 302.

As another example, the specimen validity analyzer 122 may select a physical characteristic value that is logically associated with the set of reference color component values selected at 310 in the lookup table obtained at 302. In some implementations, at 312, the specimen validity analyzer 122 further selects a specimen validity status that is logically associated with the selected set of reference color component values or the selected physical characteristic value in the obtained lookup table.

In some implementations, after assessing the at least one validity characteristic at 312, the system 100 outputs or provides information regarding the assessed at least one specimen validity characteristic via the information output device 160.

In implementations in which the specimen test article 150 includes two or more optical specimen validity markers 154, the specimen validity analyzer 122 can perform methods 200 and/or 300 with respect to each specimen validity marker 154 sequentially or in parallel.

Furthermore, although the specimen validity analyzer 122 is discussed in reference to method 300 as using a lookup table 120 to select a set of reference color component values and assess the specimen validity characteristic, in some implementation, the specimen validity analyzer 122 uses other data structures to perform such operations, including, for example, various forms of databases, indexes, computations, or other structures.

As an example, in some implementations, the specimen validity analyzer 122 may input a selected set of reference color component values into one or more analytical equations to obtain a physical characteristic value associated with such set of reference color component values. Likewise, in some implementations, the specimen validity analyzer 122 may input a determined physical characteristic value into one or more analytical equations to obtain a specimen validity status or characteristic result associated with such determined physical characteristic value.

In addition, in some implementations, the specimen validity analyzer 122 additionally performs methods similar to methods 200 and 300 of FIGS. 2 and 3 with respect to the optical test substance marker 152 to determine the presence or absence of the test substance within the specimen. For example, the specimen validity analyzer 122 or a different component of computing device 110 can determine a set of color component values for one or more pixels of an image that are representative of the optical test substance marker 152. The specimen validity analyzer 122 or a different component of computing device 110 can assess the presence or absence of a test subject substance within a sample based at least in part on each of the determined color component values. For example, the specimen validity analyzer 122 or a different component of computing device 110 can use a distance formula to compare the determined set of color component values with one or more sets of reference color component values respectively associated with different test subject substance characteristics (e.g., presence or absence). Thus, each of the techniques described above with respect to determination of specimen validity can be analogously applied to determination of the presence of the test subject substance.

Those of skill in the art will recognize that many of the methods or algorithms set out herein may employ additional acts, may omit some acts, and/or may execute acts in a different order than specified.

The various embodiments described above can be combined to provide further embodiments. To the extent that they are not inconsistent with the specific teachings and definitions herein, all of the commonly assigned U.S. patents, U.S. patent application publications, U.S. patent applications referred to in this specification, including but not limited to U.S. Provisional Patent Application No. 62/111,418, filed Feb. 3, 2015 are incorporated herein by reference, in their entirety. Aspects of the embodiments can be modified, if necessary, to employ systems, circuits and concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A specimen analysis system to analyze specimen test articles which include at least one optical test subject substance marker that indicates at least a presence or an absence of a test subject substance in a specimen, and at least one optical specimen validity marker, a color of which indicates a validity of the specimen, the specimen analysis system comprising:
   at least one processor; and
   at least one non-transitory processor-readable medium that is communicatively coupled to the at least one processor and that stores at least one of processor-executable instructions or data that, when executed by the at least one processor, cause the at least one processor to:
      receive a set of image information that represents an image of at least a specimen validity portion of the specimen test article which includes the at least one optical specimen validity marker, the color of which indicates the validity of the specimen;
      determine a set of color component values for one or more of a plurality of pixels of the image that are representative of the specimen validity portion of the specimen test article, the set of color component values comprising at least three color component values, each of the color component values representative of an amount of a respective color component of a color of the corresponding one or more of the plurality of pixels of the image; and
      assess at least one specimen validity characteristic of the specimen based at least in part on each color component value of the determined set of color component values for the one or more of the plurality of pixels of the image.

2. The specimen analysis system of claim 1 wherein to determine a set of color component values, the processor determines a red color component value, a green color component value, and a blue color component value.

3. The specimen analysis system of claim 1 wherein to assess at least one specimen validity characteristic of the specimen, the processor assesses the at least one specimen validity characteristic based at least in part on each of a red color component value, a green color component value, and a blue color component value.

4. The specimen analysis system of claim 1 wherein to assess at least one specimen validity characteristic of the specimen, the processor assesses at least a first specimen validity characteristic based at least in part on each of a first red color component value, a first green color component value, and a first blue color component value of a first one of the at least one optical specimen validity marker, and assesses at least a second specimen validity characteristic based at least in part on each of a second red color component value, a second green color component value, and a second blue color component value of a second one of the at least one optical specimen validity marker.

5. The specimen analysis system of claim 1 wherein execution of the at least one of the processor-executable instructions or data cause the at least one processor to assess the presence or the absence of one or more of oxidants, creatinine, nitrite, and aldehydes in the specimen.

6. The specimen analysis system of claim 1 wherein execution of the at least one of the processor-executable instructions or data further cause the at least one processor to:
assess the presence or the absence of the test subject substance in the specimen based at least in part on the at least one optical test subject substance marker.

7. The specimen analysis system of claim 6 wherein execution of the at least one of the processor-executable instructions or data cause the at least one processor to assess the presence or the absence of alcohol, cocaine, marijuana, amphetamines, performance enhancing drugs, substances indicative of use of alcohol, cocaine, marijuana, amphetamines, or performance enhancing drugs, or derivatives of alcohol, cocaine, marijuana, amphetamines, or performance enhancing drugs in the specimen.

8. The specimen analysis system of claim 6 wherein the specimen test article is a lateral flow strip, and the at least one optical test subject substance marker that indicates at least the presence or the absence of the test subject substance in the specimen is spaced on the lateral flow strip from the at least one optical specimen validity marker, the color of which indicates the validity of the specimen.

9. The specimen analysis system of claim 1, further comprising:
an image capture device that captures the image that depicts at least the specimen validity portion of the specimen test article, the image capture device communicatively coupled to the at least one processor.

10. The specimen analysis system of claim 1 wherein to assess at least one specimen validity characteristic, the processor determines the validity of the specimen based at least in part on each color component value of the determined set of color component values.

11. The specimen analysis system of claim 1 wherein to assess at least one specimen validity characteristic, the processor selects one of a plurality of potential values of a physical characteristic of the specimen based at least in part on each color component value of the determined set of color component values.

12. The specimen analysis system of claim 11 wherein execution of the at least one of the processor-executable instructions or data further cause the at least one processor to:
determine the validity of the specimen based at least in part on the selected one of the plurality of potential values of the physical characteristic of the specimen.

13. The specimen analysis system of claim 11 wherein the physical characteristic of the specimen comprises one or more of a pH of the specimen and a specific gravity of the specimen.

14. The specimen analysis system of claim 1 wherein the at least one non-transitory processor-readable medium further stores at least one lookup table and to assess at least one specimen validity characteristic, the processor uses the lookup table to select a value of the at least one specimen validity characteristic based at least in part on each color component value of the set of color component values.

15. The specimen analysis system of claim 1 wherein the set of color component values comprises at least a first color component value, a second color component value, and a third color component value, the at least one non-transitory processor-readable medium further stores a plurality of sets of reference color component values, each set of reference color component values comprising at least a first reference color component value, a second reference color component value, and a third reference color component value, and to assess at least one specimen validity characteristic, the processor identifies a first set of reference color component values of the plurality of sets of reference color component values that is closest to the set of color component values determined for the one or more of the plurality of pixels.

16. The specimen analysis system of claim 15 wherein to assess at least one specimen validity characteristic, the processor further assesses the at least one specimen validity characteristic based at least in part on the identified first set of reference color component values.

17. The specimen analysis system of claim 15 wherein to identify a first set of reference color component values, the processor determines a distance value for each of the plurality of sets of reference color component values and selects the set of reference color component values with the smallest distance value as the first set of reference color component values.

18. The specimen analysis system of claim 17 wherein to determine a distance value for each of the plurality of sets of reference color component values, the processor respectively inputs each of the plurality of sets of reference color component values into a distance formula with the set of color component values to determine the distance value for such set of reference color component values, the distance formula comprising a square root of a first squared difference between the first color component value and the first reference color component value of the inputted set of reference color component values plus a second squared difference between the second color component value and the second reference color component value of the inputted set of reference color component values plus a third squared difference between the third color component value and the third reference color component value of the inputted set of reference color component values.

19. The specimen analysis system of claim 15 wherein to assess at least one specimen validity characteristic, the processor further selects a value of a physical characteristic of the specimen associated with the first set of reference color component values and wherein execution of the at least one of the processor-executable instructions or data further cause the at least one processor to determine the validity of the specimen based at least in part on the selected value of the physical characteristic.

20. The specimen analysis system of claim 19 wherein to determine the validity of the specimen, the processor selects a specimen validity status associated with the selected value of the physical characteristic in a lookup table.

21. A computer-implemented method to analyze specimen test articles which include at least one optical test subject substance marker that indicates at least a presence or an absence of a test subject substance in a specimen, and at least one optical specimen validity marker, a color of which indicates a validity of the specimen, the method comprising:
receiving, by one or more computing devices, a set of image information that represents an image of at least a specimen validity portion of the specimen test article which includes the at least one optical specimen validity marker, the color of which indicates the validity of the specimen;
determining, by the one or more computing devices, a set of color component values for one or more of a plurality of pixels of the image that are representative of the specimen validity portion of the specimen test article, the set of color component values comprising at least three color component values, each of the color component values representative of an amount of a respective color component of a color of the corresponding one or more of the plurality of pixels of the image; and assessing, by the one or more computing devices, at least one specimen validity characteristic of the specimen based at least in part on each color component value of the determined set of color component values for the one or more of the plurality of pixels of the image.

22. The computer-implemented method of claim 21 wherein determining a set of color component values comprises determining, by the one or more computing devices, a red color component value, a green color component value, and a blue color component value.

23. The computer-implemented method of claim 21 wherein assessing at least one specimen validity characteristic comprises assessing, by the one or more computing devices, the at least one specimen validity characteristic based at least in part on each of a red color component value, a green color component value, and a blue color component value.

24. The computer-implemented method of claim 21 wherein assessing at least one specimen validity characteristic comprises assessing, by the one or more computing devices, at least a first specimen validity characteristic based at least in part on each of a first red color component value, a first green color component value, and a first blue color component value of a first one of the at least one optical specimen validity marker, and assessing, by the one or more computing devices, at least a second specimen validity characteristic based at least in part on each of a second red color component value, a second green color component value, and the second blue color component value of a second one of the at least one optical specimen validity marker.

25. The computer-implemented method of claim 21 wherein assessing at least one specimen validity characteristic comprises assessing, by the one or more computing devices, the presence or the absence of one or more of oxidants, creatinine, nitrite, and aldehydes in the specimen.

26. The computer-implemented method of claim 21, further comprising:

assessing, by the one or more computing devices, the presence or the absence of the test subject substance in the specimen based at least in part on the at least one optical test subject substance marker.

27. The computer-implemented method of claim 26 wherein assessing the presence or absence of the test subject substance comprises assessing, by the one or more computing devices, the presence or absence of one or more of alcohol, cocaine, marijuana, amphetamines, performance enhancing drugs, substances indicative of use of alcohol, cocaine, marijuana, amphetamines, or performance enhancing drugs, or derivatives of alcohol, cocaine, marijuana, amphetamines, or performance enhancing drugs in the specimen.

28. The computer-implemented method of claim 26 wherein receiving the set of image information comprises receiving, by the one or more computing devices, the set of image information that represents the image of at least the specimen validity portion of a lateral flow strip, and the at least one optical test subject substance marker that indicates at least the presence or the absence of the test subject substance in the specimen is spaced on the lateral flow strip from the at least one optical specimen validity marker, the color which indicates the validity of the specimen.

29. The computer-implemented method of claim 21, further comprising:

capturing, by an image capture device, the image that depicts at least the specimen validity portion of the specimen test article.

30. The computer-implemented method of claim 21 wherein assessing at least one specimen validity characteristic comprises determining, by the one or more computing devices, the validity of the specimen based at least in part on each color component value of the determined set of color component values.

31. The computer-implemented method of claim 21 wherein assessing at least one specimen validity characteristic comprises selecting, by the one or more computing devices, one of a plurality of potential values of a physical characteristic of the specimen based at least in part on each color component value of the determined set of color component values.

32. The computer-implemented method of claim 31, further comprising:

determining, by the one or more computing devices, the validity of the specimen based at least in part on the selected one of the plurality of potential values of the physical characteristic of the specimen.

33. The computer-implemented method of claim 31 wherein selecting one of a plurality of potential values of a physical characteristic of the specimen comprises selecting, by the one or more computing devices, one of a plurality of potential pH values of the specimen or selecting, by the one or more computing devices one of a plurality of potential specific gravity values of the specimen.

34. The computer-implemented method of claim 21 wherein assessing at least one specimen validity characteristic comprises using, by the one or more computing devices, a lookup table to select a value of the at least one specimen validity characteristic based at least in part on each color component value of the determined set of color component values.

35. The computer-implemented method of claim 21 wherein determining a set of color component values comprises determining, by the one or more computing devices, at least a first color component value, a second color component value, and a third color component value, and assessing at least one specimen validity characteristic comprises identifying, by the one or more computing devices, a first set of reference color component values from a plurality of sets of reference color component values that is closest to the set of color component values determined for the one or more of the plurality of pixels, each set of reference color component values comprising at least a first reference color component value, a second reference color component value, and a third reference color component value.

36. The computer-implemented method of claim 35 wherein assessing the at least one specimen validity characteristic further comprises assessing, by the one or more computing devices, the at least one specimen validity characteristic based at least in part on the identified first set of reference color component values.

37. The computer-implemented method of claim 35 wherein identifying a first set of reference color component values comprises determining, by the one or more computing devices, a distance value for each of the plurality of sets of reference color component values and selecting, by the one or more computing devices, the set of reference color component values with the smallest distance value as the first set of reference color component values.

38. The computer-implemented method of claim 37 wherein determining a distance value comprises respectively inputting, by the one or more computing devices, each of the plurality of sets of reference color component values into a distance formula with the set of color component values to determine the distance value for such set of reference color component values, the distance formula comprising a square root of a first squared difference between the first color component value and the first reference color component value of the inputted set of reference color component values plus a second squared difference between the second color component value and the second reference color component value of the inputted set of reference color component values plus a third squared difference between the third color component value and the third reference color component value of the inputted set of reference color component values.

39. The computer-implemented method of claim 35 wherein assessing the at least one specimen validity characteristic further comprises selecting, by the one or more computing devices a value of a physical characteristic of the specimen associated with the first set of reference color component values and determining, by the one or more computing devices, the validity of the specimen based at least in part on the selected value of physical characteristic.

40. The computer-implemented method of claim 39 wherein determining the validity of the specimen comprises selecting, by the one or more computing devices, a specimen validity status associated with the selected value of the physical characteristic a lookup table.

\* \* \* \* \*